US008834702B2

(12) United States Patent
Lin et al.

(10) Patent No.: US 8,834,702 B2
(45) Date of Patent: Sep. 16, 2014

(54) BIOSENSOR AND USAGE THEREOF

(75) Inventors: Jinn-Nan Lin, San Diego, CA (US); Chia-Lin Wang, San Diego, CA (US); Ziyi Zhang, Hangzhou (CN)

(73) Assignee: Leadway (HK) Limited, Hong Kong (HK)

(*) Notice: Subject to any disclaimer, the term of this patent is extended or adjusted under 35 U.S.C. 154(b) by 333 days.

(21) Appl. No.: 13/320,903

(22) PCT Filed: May 24, 2010

(86) PCT No.: PCT/CN2010/073147
§ 371 (c)(1),
(2), (4) Date: Nov. 16, 2011

(87) PCT Pub. No.: WO2010/135978
PCT Pub. Date: Dec. 2, 2010

(65) Prior Publication Data
US 2012/0061259 A1   Mar. 15, 2012

(30) Foreign Application Priority Data

May 25, 2009  (CN) .......................... 2009 1 0142768

(51) Int. Cl.
*G01N 27/327* (2006.01)
*G01N 33/543* (2006.01)
*C12Q 1/00* (2006.01)

(52) U.S. Cl.
CPC ............ *G01N 33/5438* (2013.01); *C12Q 1/005* (2013.01); *G01N 27/3272* (2013.01)
USPC .................... 205/777.5; 205/792; 204/403.01

(58) Field of Classification Search
USPC .............. 204/403.01–403.15; 205/777.5, 792
See application file for complete search history.

(56) References Cited

U.S. PATENT DOCUMENTS

| 5,120,420 A | 6/1992 | Nankai et al. |
| 5,141,868 A | 8/1992 | Shanks et al. |
| 5,192,415 A | 3/1993 | Yoshioka et al. |

(Continued)

FOREIGN PATENT DOCUMENTS

| CN | 1122178 C | 9/2003 |
| CN | 1461410 A | 12/2003 |

(Continued)

OTHER PUBLICATIONS

International Search Report issued in PCT/CN2010/073147 dated Sep. 2, 2010.

*Primary Examiner* — J. Christopher Ball
(74) *Attorney, Agent, or Firm* — Michael A. Whittaker; Acuity Law Group, P.C.

(57) ABSTRACT

A biosensor for quantifying an analyte in a sample and usage thereof are provided. The biosensor includes an insulative substrate, a cover, a sample supply port, an electrode system including at least a working electrode, a counter electrode and a third electrode, and a reaction layer at least formed over the working electrode. The third electrode, used for estimating whether the amount of the sample is sufficient, is disposed nearer to the sample supply port than the counter electrode is. Whether the amount of the added sample is sufficient is estimated by comparing the electrical current value detected between the working electrode and the counter electrode with the electrical current value detected between the working electrode and the third electrode. This invention has a simple structure and produces accurate measurements.

10 Claims, 10 Drawing Sheets

(56) References Cited

U.S. PATENT DOCUMENTS

| | | | |
|---|---|---|---|
| 5,320,732 A | | 6/1994 | Nankai et al. |
| 5,582,697 A | * | 12/1996 | Ikeda et al. ............... 205/777.5 |
| 6,340,428 B1 | | 1/2002 | Ikeda et al. |
| 6,531,040 B2 | | 3/2003 | Musho et al. |
| 6,790,327 B2 | | 9/2004 | Ikeda et al. |
| 2004/0079653 A1 | | 4/2004 | Karinka et al. |
| 2010/0243481 A1 | * | 9/2010 | Bae et al. ..................... 205/792 |
| 2010/0300898 A1 | * | 12/2010 | Sato et al. ..................... 205/792 |

FOREIGN PATENT DOCUMENTS

| | | | |
|---|---|---|---|
| CN | 1607387 A | | 4/2005 |
| CN | 100356168 C | | 12/2007 |
| EP | 0987544 B1 | | 10/2007 |
| JP | 11-344462 A | | 12/1999 |
| JP | 3267933 B2 | | 3/2002 |
| WO | WO 2009/057793 | * | 5/2009 |

\* cited by examiner

BIOSENSOR AND USAGE THEREOF

This application is a national stage filing of PCT Application Serial No. PCT/CN2010/073147, filed May 24, 2010 (now published as WO 2010/135978), and claims the benefit of Chinese patent application Serial No. 200910142768.1, filed May 25, 2009, each of which is hereby incorporated by reference in their entireties, including all tables, figures, and claims.

FIELD OF THE INVENTION

This invention is related to a biosensor for analyzing specific components of a sample liquid and methods of use thereof.

BACKGROUND OF THE INVENTION

In recent years, medical care has changed dramatically, from primarily using clinical laboratory analysis of samples to rapid point of care testing in the doctor's office or at the patient's bedside. Disposable enzyme biosensors are frequently used to perform these rapid tests. Taking glucose testing as an example, in-home testing by the patient is now commonplace and a necessity for proper disease management. To conduct an in-home test using a glucose biosensor, the diabetic patient lances the finger to withdraw a small amount of blood. The patient applies the blood to the biosensor test strip and the meter accompanying the biosensor records electrical data from the biosensor and calculates the glucose concentration in the patient's blood within a few seconds. This information is used to make decisions about when and how much insulin to be used.

Various types of biosensors utilizing a specific catalysis of an enzyme have been developed. Recently mostly biosensor utilizes an electrochemical method, such as meter for measuring glucose. Usually a biosensor comprises an anode electrode and a cathode electrode formed on an insulating substrate in the electrochemical method, and the reaction layer is formed on the electrodes. When a sample is disposed into the biosensor, the target substance of the sample will make redox reactions in enzyme catalysis. Oxygen carriers or mediators are reduced. The reduced oxygen carriers or the reduced mediators are oxidized due to the electrode potential, releasing electrons and lead to change in the electron. That is the electrochemical method to detection the concentration of the substances in the sample indirectly through such electronic changes. For example, U.S. Pat. Nos. 5,120,420 and 5,320,732 to Nankai, U.S. Pat. No. 5,141,868 to Shanks disclose disposable glucose biosensors. These biosensors are constructed of two plastic layers laminated to spacers and thereby held together. This structure forms a vented capillary channel that draws an applied sample into the interior and onto a test area. When the sample flows into the channel by capillary flow, the sample comes into contact with an enzyme layer and electrodes, which detect and optionally measure an analyte in the sample.

For other example, U.S. Pat. No. 5,192,415 discloses a biosensor comprising a working electrode and a counter electrode which are formed on the insulating substrate, a reaction provided on the electrodes. Quantifying a substrate contained in a sample liquid using a reaction of the substrate to enzyme in the electrode system, such as glucose concentration of the blood sample. But when the sample is not enough, test procedure is still carried out. Therefore, the sample often can not completely cover the working electrode resulting in the inaccurate test results. In order to overcome the disadvantage, U.S. Pat. No. 5,582,697 disclosed a third electrode for detecting whether the sample is enough. U.S. Pat. No. 5,582,697 disclosed the third electrode is disposed farther from a sample introducing port than the working electrode and the counter electrode. The current is measured when the sample reaches the third electrode, indicating the sample has completely covered the working electrode and the count electrode. At this time, measuring the concentration of analytes in the sample will be started. Otherwise, a warning of the sample not enough will be showed.

However, the distance of the third electrode in U.S. Pat. No. 5,582,697 is particularly important. If the third electrode is too close, the flow front behavior of the added sample will present not a line for the capillary action during the sample flow into the biosensor. If when the flow front behavior becomes a concave or a convex, the phenomenon could occur that the test will be started when the sample arrive the third electrode but the sample does not completely cover the working electrode. If the third is designed too far distance, that could ensure the sample completely covering the working electrode, but this design requires more samples, for example, it will need more blood sample from patient that will result in more pain for patient.

SUMMARY OF THE INVENTION

In order to overcome the above disadvantages, the present invention provides a biosensor that is simply manufacturable and performs accurate measurements.

A biosensor of the present invention includes an insulative substrate with an electrode system, a reaction layer covering at least one electrode of the electrode system, a covering layer and a sample introducing port. The electrode system at least includes a working electrode, a counter electrode and a third electrode, wherein the third electrode, which is used to estimate if the amount of sample to be tested is sufficient, is nearer to the sample introducing port than the counter electrode. In one embodiment, the working electrode is located between the counter electrode and the third electrode. In another embodiment, the working electrode is the nearest to the sample introducing port, while the counter electrode is the farthest to the sample introducing port.

This invention further provides a method of using the biosensor of the invention to estimate if an amount of sample liquid is sufficient. The method includes: providing a biosensor including an insulative substrate with an electrode system/thereon, a reaction layer covering at least one electrode of the electrode system, a covering layer and a sample introducing port, the electrode system at least including a working electrode, a counter electrode and a third electrode used in estimating if an amount of sample liquid to be tested is sufficient, wherein the third electrode is nearer to the sample introducing port than the counter electrode; applying a sample liquid to the biosensor and detecting the current value 1 between the working electrode and the counter electrode and the current value 2 between the working electrode and the third electrode; comparing the values of the current 1 and the current 2, then estimating if the amount of the supplied sample liquid is sufficient to fulfil the test requirement. In one embodiment, when the value of the detected current 1 is zero or an ultra low value, it means the supplied sample liquid for test is insufficient, and the measuring meter will display that the test is invalid. The ultra low value is defined under specific experiments, such as the value of current detected from a blood sample whose glucose concentration is zero. In another embodiment, it is estimated by comparing the absolute values of the current 1 and the current 2 if the amount of the applied sample liquid sufficiently fulfils the test requirement. In a further embodiment, it is estimated by comparing the bias of the current value 1 and the current value 2 if the amount of the applied sample liquid sufficiently fulfils the test requirement.

The present invention further provides a method of using the biosensor of the invention to detect the concentration of an analyte of interest in the sample liquid. The method includes: applying a sample liquid to a sample introducing port of a biosensor; inserting the biosensor into an electrical detecting system and connecting the biosensor with the electrical detecting system via the connecting conductors; detecting the current value 1 between the working electrode and the counter electrode and the current value 2 between the working electrode and the third electrode; comparing the values of the current 1 and the current 2 with a predetermined threshold, if it is estimated that the volume of applied sample liquid cannot fulfil the testing requirement, outputting an error of insufficient sample; if it is estimated that the volume of applied sample liquid can fulfil the testing requirement, the electrical detecting system will output the concentration of the analyte of interest in the tested sample liquid. In one embodiment, to compare the bias, or rate of the bias, between the values of the current 1 and the current 2, if the bias or the rate of the bias is greater than a predetermined threshold, it indicates that supplied sample liquid is insufficient, and the meter will output an information of insufficient sample; if the rate of the bias is less than or equal to a predetermined threshold, converting the value of the current 1 detected between the working electrode and the counter electrode into percentage of the substrate to be detected in the tested sample.

Advantages of the present invention includes: since the third electrode, which is used to estimate if the supplied sample liquid is sufficient, is nearer to the sample introducing port than the counter electrode, when the amount of the applied sample cannot fulfil the predetermined test requirement, the bias of the electrical parameter between the two groups of electrode circuits is very large, it is much easier to be recognized by the electrical detecting system with less error. So, by switching between the two groups of electrical circuits, and comparing the electrical parameters of the two groups of electrical circuits, it can be more sensitively and precisely estimated if the applied amount of the sample liquid fulfils the test requirement, thereby making the test results more precise. Furthermore, by using the electrical parameters of the two groups of electrical circuits to estimate the amount of the applied sample liquid and the time for initiating a test, it can effectively shorten the distance between the electrodes, therefore shorten the paths that the sample liquid travels on the biosensor. So, it requires less sample liquid and causes less pain to the testers and effectively shortens the test time and outputs the test result more quickly.

DETAILED DESCRIPTION OF EMBODIMENTS

Figure 1:
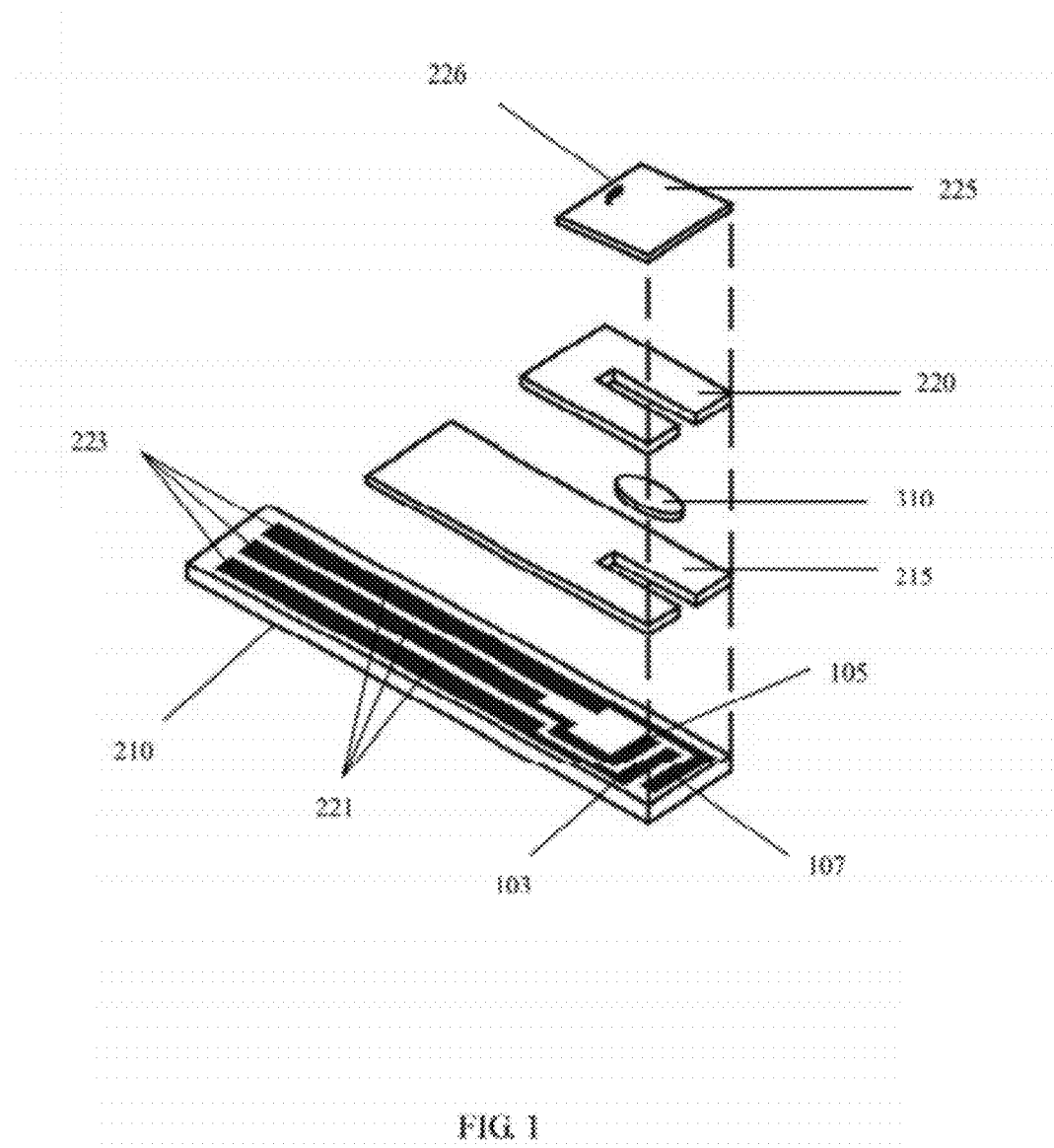
FIG. 1 is an exploded view of the biosensor of the present invention.

A biosensor 100 of the present invention includes an insulative substrate 210 with an electrode system thereon, a reaction layer 310 at least located on a working electrode 103 of the electrode system, a covering layer 225 and a sample introducing port 224. The above elements can be laminated together or stuck by glue. The biosensor 100 can also be formed by printing on the substrate.

Referring to FIG. 1, the insulative substrate 210 includes an electrode system used to detect the existence or concentration of analytes of interest in the sample liquid. The electrode system has at least three electrodes and a corresponding number of electrode conducts, but can also has more than three electrodes and a corresponding number of electrode conducts. The substrate 210 can be formed by a variety of materials, such as carbon, polystyrene, polycarbonate, polyvinyl chloride resin, and polyester. In one embodiment the base layer is constructed of polyethylene terephthalate (PET). The thickness is 3-10 mil, for example, a strip of PET 5 mil thick (mil, mil, unit of length, 1 mil equals one thousandth of inch, that is 0.0254 mm) provides an appropriate support, as does a 14 mil white film PET. Of course many different thicknesses will also function well in the invention. The substrate provides a support for receiving the electrodes and electrode leads.

In a particular embodiment, the electrodes and electrode leads are printed on the insulative substrate. Ag/AgCl, carbon inks (graphite), palladium, gold, platinum, iridium, doped indium tin oxide, stainless steel, and other suitable conducting materials can be used. The electrodes and electrode leads can be produced with the same material or different materials. The graphite is very suitable to make electrodes for its big pore and good adsorbability. Electrodes can also be made by the combination of these materials. For example, one part of the electrode utilizes one material, while the other part of the electrode utilizes the other material.

Figure 2:
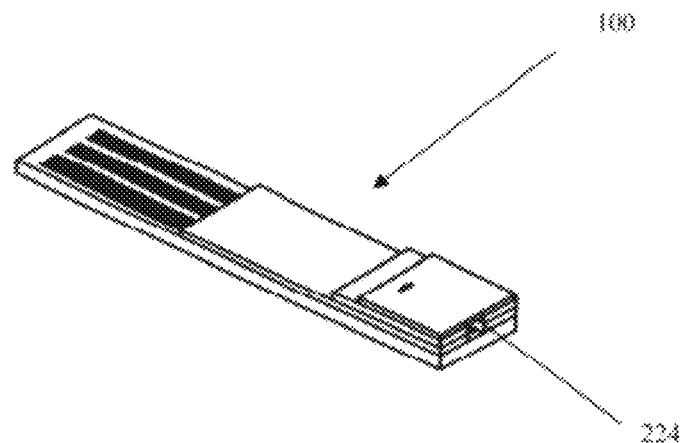
FIG. 2 is a schematic view of the biosensor of the present invention.

As illustrated in FIGS. 1 and 2, the electrode system of the insulative substrate includes a working electrode 103, a counter electrode 105 and a third electrode 107 for estimating if an amount of the supplied sample liquid to be tested is sufficient. The third electrode 107 is nearer to the sample introducing port than the counter electrode 105. In one embodiment, the third electrode 107 is the nearest to the sample introducing port 224, and the counter electrode 105 is the farthest to the sample introducing port 224, and the working electrode 103 is located between the counter electrode 105 and the third electrode 107. In another embodiment, the working electrode 103 is the nearest to the sample introducing port 224, the counter electrode 105 is the farthest to the sample introducing port 224, and the third electrode 107 is located between the worker electrode 103 and the counter electrode 105. But the working electrode 103 cannot be located farthest to the sample introducing port. The insulative substrate 210 further includes electrode conducts 221 with connecting conducts 223 at one end of the electrode conducts 221. The connecting conducts 223 are used to connect the biosensor with an electrical detecting system. The electrical detecting system detects, via the connecting conducts, the current produced by the reaction on the biosensor and calculates the existence or concentration of the analyte of interest in the sample liquid. The insulative layer 215 covers the electrode system but leaves a hole at a front end thereof above the electrode system. The reaction layer 310 locates in the hole in the insulative layer and covers the electrode system, therefore forms a reaction room.

The reaction layer 310 locates on at least one of the electrodes, but can also cover two or all of the electrodes. The reaction layer contains one or more reagents for measuring the presence or concentration of an analyte of interest in the fluid sample. In one embodiment the reaction layer contains an oxidoreductase and an electron acceptor, for analyzing the sample and generating a substance through the reaction that is detectable by the electrode system.

In one embodiment, there is a gap layer 220 between the insulative layer 215 and the covering layer 225. The gap layer 220 has a sample introducing port 224 at a corresponding area above the reaction layer. The gap layer can be formed by adhesive materials.

In one embodiment the analyte of interest is glucose present in blood. In this embodiment, the reaction layer can include glucose oxidoreductase and the electron transport carriers. The reagents can also include a binder. In one embodiment the binder is hydroxyethylcellulose (HEC). This binder is hydrophilic and can also be used to mix with the incoming blood sample so that an electrochemical cell is established in a period of seconds. Other materials can also be used as the binder, for example, hydroxymethylcellulose and hydroxypropylcellulose. A stabilizer can also be included in the reagent formulation. In one embodiment polyethylene glycol (PEG) can be included. PEG can also facilitate a rapid response in the assay. In various other embodiments the reaction layer can also contain mediators, surfactants, stabilizers, and polymers, and any other reagents that are useful for conducting the assay.

The present invention could measure any analytes which can be measured by electrochemical method. For example, glucose, lactate, urea, bicarbonate, 3-hydroxybutyric acid (3-HBA), amino acids (e.g., L-glutamate, aspartate, L-lysine), ammonium, sodium, calcium, trace metals, and any other analyte for which there can be designed an electrochemical assay. The reagents in the reaction layer will of course be changed to those appropriate for testing for the analyte of interest. When 3-HBA is the analyte, mediators such as K3Fe(CN)6, ferrocene, hexacyanoferrate, and enzymes such as 3-HBA dehydrogenase and diaphorase, and the cofactor NAD can be included in the reaction layer.

Any sample fluid sample or fluidized sample can be analyzed using the devices. Examples of sample fluids that can be tested include whole blood, blood serum, blood plasma, urine, and saliva. Clinical samples, biological samples, and environmental samples can also be tested, whether they are supplied as fluids or must be liquefied before analysis. The sample fluid can also be a buffer, or a solution or suspension containing a solid or gaseous biological material.

The present biosensors and methods can be used to qualitatively or quantitatively detect any analyte or enzyme. For example, the analyte to be assayed can be macromolecules such as peptides, proteins, e.g., antibodies or receptors, oligonucleotides, nucleic acids, vitamins, oligosaccharides, carbohydrates, lipids, or small molecules, or a complex thereof. Exemplary proteins or peptides include enzymes, transport proteins such as ion channels and pumps, nutrient or storage proteins, contractile or motile proteins such as actins and myosins, structural proteins, defense proteins or regulatory proteins such as antibodies, hormones and growth factors. Exemplary nucleic acids include DNA, such as A-, B- or Z-form DNA, and RNA such as mRNA, tRNA and rRNA. The nucleic acids can be single-, double- and triple-stranded nucleic acids. Exemplary vitamins include water-soluble vitamins such as thiamine, riboflavin, nicotinic acid, pantothenic acid, pyridoxine, biotin, folate, vitamin B12 and ascorbic acid, and fat-soluble vitamins such as vitamin A, vitamin D, vitamin E, and vitamin K. Exemplary lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

The analyte or enzyme to be detected may be a marker for a biological pathway, a stage of cell cycle, a cell type, a tissue type, an organ type, a developmental stage, a disease, disorder or infection type or stage, or drug or other treatments. Exemplary tissues include connective, epithelium, muscle or nerve tissues. Exemplary organs include an accessory organ of the eye, annulospiral organ, auditory organ, Chievitz organ, circumventricular organ, Corti organ, critical organ, enamel organ, end organ, external female genital organ, external male genital organ, floating organ, flower-spray organ of Ruffini, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmuller, sense organ, organ of smell, spiral organ, subcommissural organ, subformical organ, supernumerary organ, tactile organ, target organ, organ of taste, organ of touch, urinary organ, vascular organ of lamina terminals, vestibular organ, vestibulocochlear organ, vestigial organ, organ of vision, visual organ, vomeronasal organ, wandering organ, Weber organ and organ of Zuckerkandl. Exemplary internal animal organs include brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels. Exemplary diseases or disorders include neoplasm (neoplasia), cancers, immune system diseases or disorders, metabolism diseases or disorders, muscle and bone diseases or disorders, nervous system diseases or disorders, signal diseases or disorders, transporter diseases or disorders In one embodiment, at least the inner surface of the cover layer 225 is formed by the hydrophilic material. The cover layer has a vent 226, which allows the communication of air between the reaction chamber and the exterior of the device.

The vent can be a groove, but in other embodiments the vent can be any shapes that allow the passage of air from the reaction chamber out of the device. The vent can be located above the spacer layer. In some embodiments, the cover layer can be a dielectric ink, which can be printed onto the biosensor. The cover layer can also contain an adhesive to affix it to the hydrophobic protective layer (if present), the insulating layer 215 and the substrate.

In one embodiment, the current invention involves a method of using the above biosensor to estimate if the supplied sample liquid to be tested is sufficient. During the testing of a sample liquid, after inserting the biosensor into an electrical detecting system, applying the sample liquid into the sample introducing port 224, the sample liquid is introduced to the electrode system of the biosensor by capillary action or other ways, and reacts with the reagents on the reaction layer.

Figure 3:
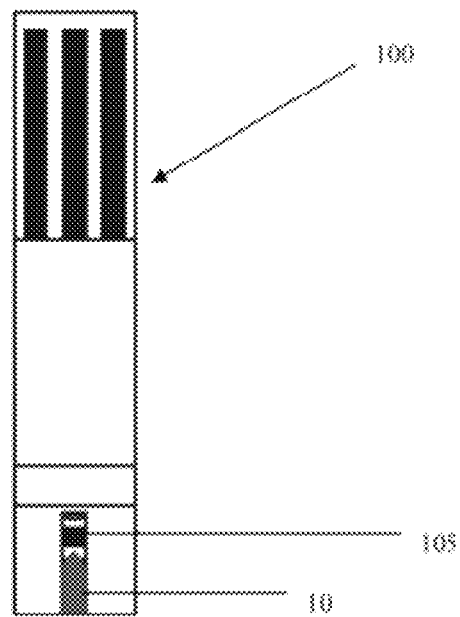
FIG. 3 is a schematic plan view of sample covering the electrodes, while the applied sample cannot reach the counter electrode.
Figure 4:
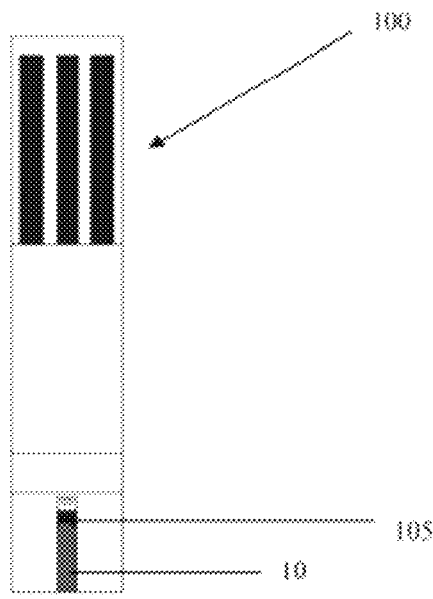
FIG. 4 is a schematic plan view of sample covering the electrodes, while the applied sample partially covers the counter electrode.
Figure 5:
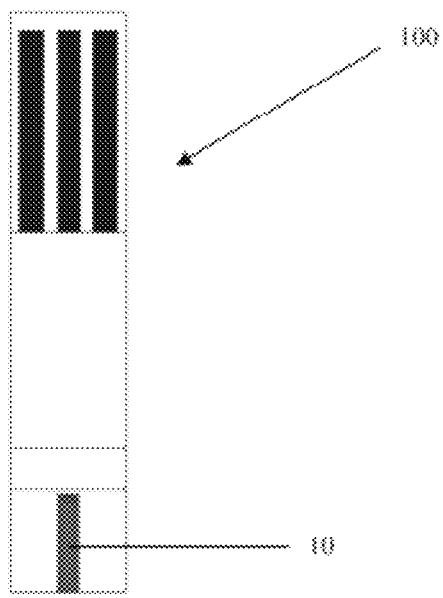
FIG. 5 is a schematic plan view of sample covering the electrodes, while the amount of the applied sample liquid is sufficient.
Figure 6:
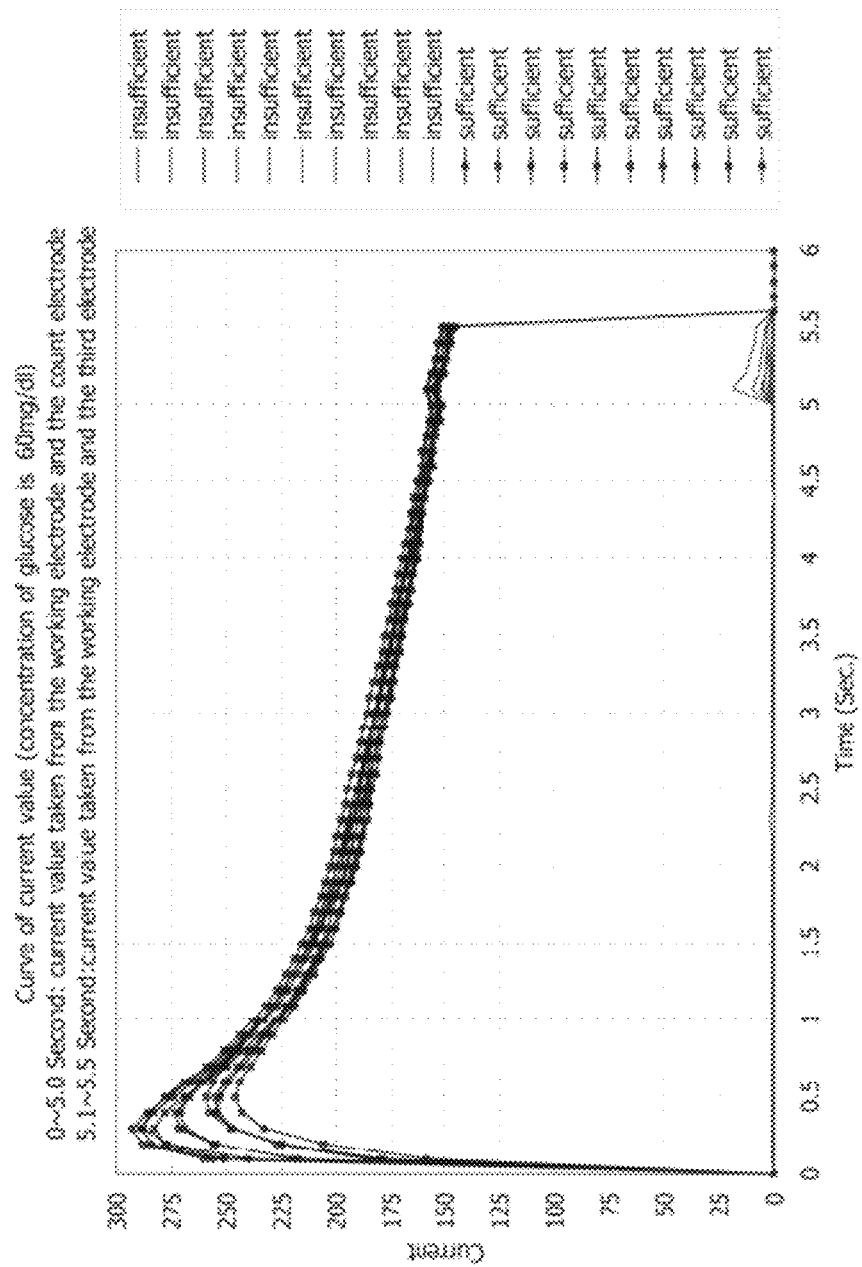
FIG. 6 is a graph showing changes in response current when the concentration of glucose is 60 mg/dl.
Figure 7:
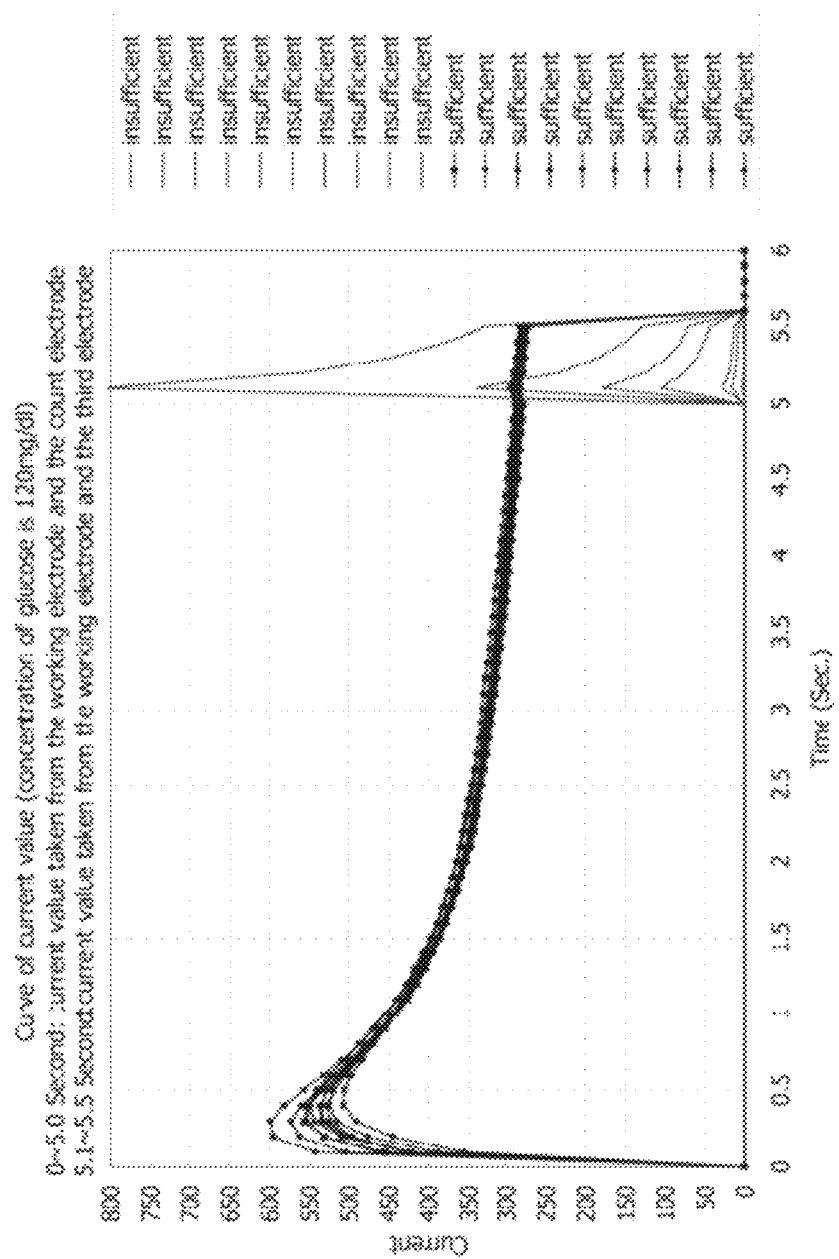
FIG. 7 is a graph showing changes in response current when the concentration Of glucose is 120 mg/dl.
Figure 8:
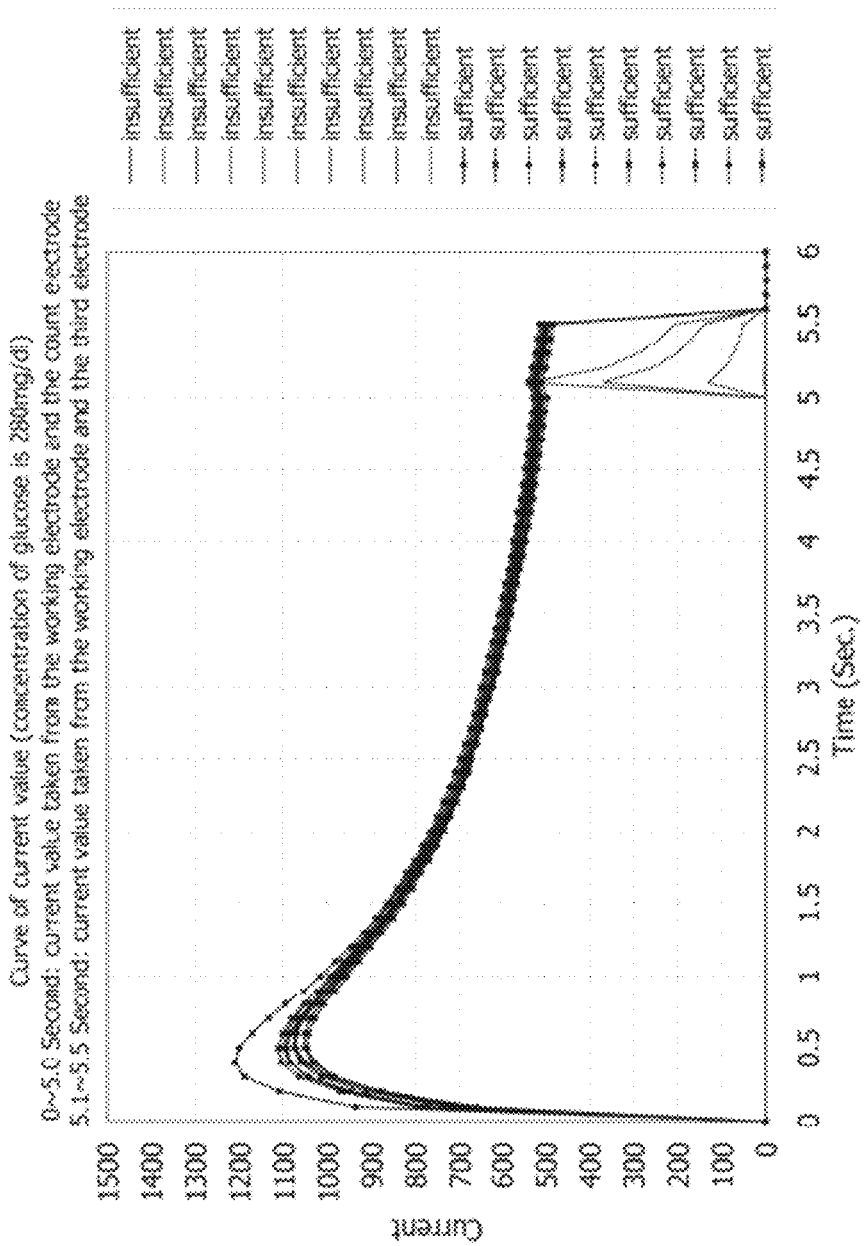
FIG. 8 is a graph showing changes in response current when the concentration of glucose is 280 mg/dl.
Figure 9:
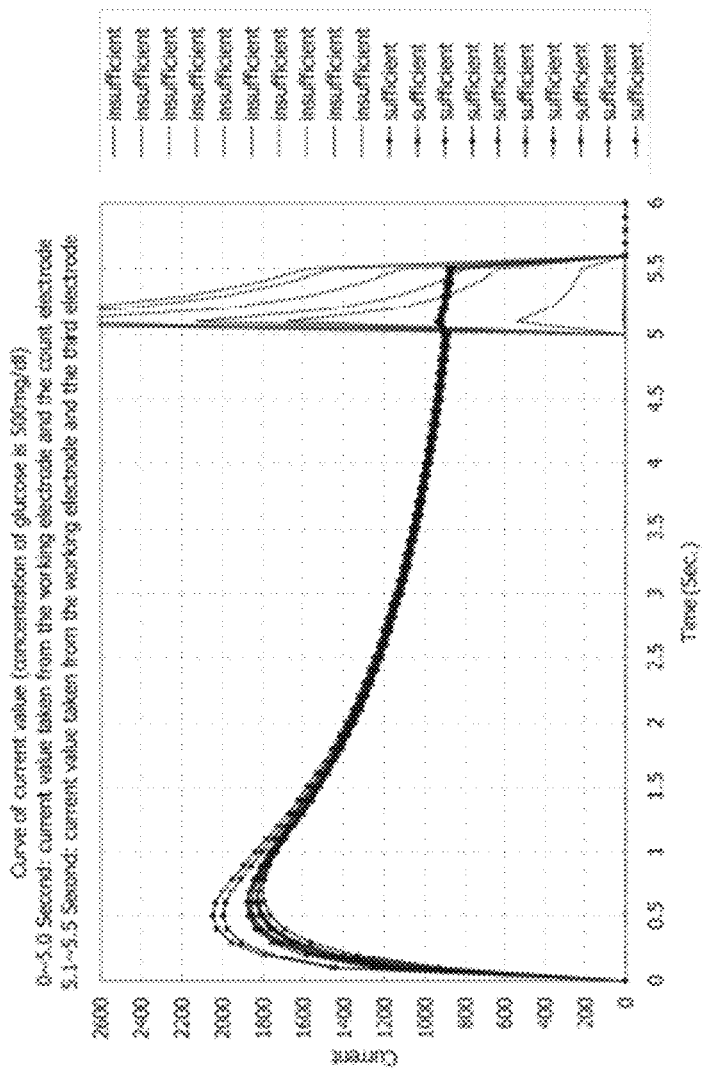
FIG. 9 is a graph showing changes in response current when the concentration of glucose is 500 mg/dl.

Due to different amounts of sample liquid being applied, there are various conditions that the sample liquid moves in the biosensor. If the amount of the applied sample liquid cannot meet the test requirement, within the predetermined testing time, the sample liquid 10 cannot reach the counter electrode (as indicated in FIG. 3) or only covers a part of the counter electrode (as indicated in FIG. 4). Under such a condition, it will happen that the amount of sample liquid applied onto the working electrode cannot achieve the covering area requirement for test, therefore renders the test result inaccurate. If the applied sample liquid is sufficient, as indicated in FIG. 5, the sample liquid 10 fully covers the counter electrode which is the farthest from the sample applying port, under such a condition, the sample liquid must cover all the area of the counter electrode for test.

In an embodiment, when the applied sample liquid is very poor, the sample liquid cannot reach the counter electrode 105. When a voltage is applied between the working electrode 103 and the counter electrode 105, the detected current is zero, and the electrical testing system will display an invalid test and inform the operator that insufficient sample liquid is applied.

In another embodiment, when the applied sample liquid can only cover a part of the counter electrode 105, then the third electrode 107, which is nearer to the sample apply port than the counter electrode 105, has been fully covered by the sample liquid. The reaction rate between the working electrode 103 and the third electrode 107 has become the largest, but the reaction rate between the working electrode 103 and the counter electrode 105 may not become the largest. Therefore, if the sample liquid is insufficient, when detecting the current 1 (I1) between the working electrode 103 and the counter electrode 105, the area that the sample liquid covers the counter electrode is insufficient to make the final reaction rate on the working electrode become the largest reaction rate, therefore intermediate product accumulates on the working electrode. If the third electrode is fully covered by the sample liquid, when the voltage is switched to the working electrode 103 and the third electrode 107 to test the current 2 (I2), the final reaction on the working electrode will become the largest, plus the intermediate product accumulated during testing the current I1, which makes the instant current value (I2) between the working electrode and the third electrode obviously increased comparing with the current value between the working electrode and the counter electrode prior to the switching. Thus, when switching from detecting the current value 1 (I1) between the working electrode 103 and the counter electrode 105 to detecting the current value 2 (I2) between the working electrode 103 and the third electrode 107, the two current values (I1 and I2) presents an obvious change, in other words, the current value I2 is obviously higher than the current value I1. In one embodiment, when the absolute bias between the current value I1 and the current value I2 is larger than a predetermined threshold, the electrical detecting system outputs a message that the applied sample liquid is insufficient. In another embodiment, when the rate of absolute bias between the current value I1 and the current value I2 is larger than a predetermined threshold, the electrical detection system outputs a message that the applied sample liquid is insufficient.

In another embodiment, if the applied sample liquid is sufficient, within a predetermined time, the sample liquid covers enough area on the counter electrode 105, thus the area that the sample liquid covers on the working electrode also achieves the testing requirement. In this condition, the reaction rate between the working electrode 103 and the counter electrode 105 becomes the largest, and the detected current value I1 equals to the current value I2 between the working electrode 103 and the third electrode 107, or the bias is very small. If the absolute bias, or the absolute bias rate, between the current value I1 and the current value I2 is smaller than a predetermined threshold, the electrical detecting system estimates that the amount of the sample liquid applied onto the biosensor meets the test requirement.

Many methods can be adopted to compare the current value 1 and the current value 2, thereby making a judgment if the amount of the applied sample liquid is sufficient. In one embodiment, within a predetermined time for estimating, if the sample liquid for test cannot reach the counter electrode 105 or the sample liquid covers only a slight part of the counter electrode 105, the current value 1 is zero or ultra low, then outputs a judgment that the supplied sample liquid is insufficient.

In another embodiment, within a predetermined time for judging, to calculate the absolute bias A between the current value 1 (I1) and the current value 2 (I2) by the formula I, and to compare the absolute bias A with the predetermined threshold, thereby estimating if the applied sample liquid is sufficient. When the absolute bias is larger than the predetermined threshold, it is estimated that the applied amount of sample liquid cannot meet the testing requirement. In an embodiment, the predetermined threshold is 10. When the absolute bias A is larger than 10, it is estimated that the supplied sample liquid is insufficient.

In one embodiment, within a predetermined time for judging, a judgment is made by comparing the absolute bias rate of the two current values with a predetermined threshold. The absolute bias rate is obtained by the formulate II. In other words, the absolute bias rate B is obtained by making the absolute bias of the current value 1 and the current value 2 and making the absolute bias divided by either the current value 1 or the current value 2. When the absolute bias rate is larger than the predetermined threshold, it is estimated that the amount of sample liquid cannot satisfy the testing requirement, and the electrical detecting system outputs a message of wrong operation. When the absolute bias rate is less than the predetermined threshold, it is estimated that the amount of sample liquid can satisfy the test requirement, and the electrical detecting system outputs accurately the concentration of the analyte of interest. In one embodiment, the predetermined threshold is 5%. When the absolute bias rate B is larger than 5%, it is estimated that the supplied sample liquid is insufficient. According to different detecting systems, the predetermined threshold can be 30%, 20% or 10% et al.

$$A - [11 - 12] \quad \text{Formulate I}$$

$$B = \frac{[11 - 12]}{11} \times 100\% \text{ or } B = \frac{[11 - 12]}{12} \quad \text{Formulate II}$$

The predetermined thresholds, as a contrastive parameter, are obtained by a series of experiments during the product design. In one embodiment, selecting various of samples liquid with different concentrations of the analyte of interest, and to perform the tests of the concentrations of the analyte of interest with different reagent formulations, different temperatures, and different interfering substances. When the amounts of sample liquid are sufficient, the experiments will get a series of biases between the current values 1 and the current values 2, or the bias rates between the current values 1 and the current values 2, which are marked by A1, A2 ... An. When the amounts of sample liquid are insufficient, the experiments will get a series of biases between the current values 1 and the current values 2, or the bias rates between the current values 1 and the current values 2, which are marked by B1, B2 ... Bn. By probability statistics method, the predetermined thresholds are limited within the range of larger than the largest in A and less than the least in B. Commonly, the selections of proper predetermined thresholds depend on the inherent variability of the test processes, the accuracies that the designers expect and the legal requirements et al. Different reaction systems and different measuring methods may get different predetermined thresholds adapted for such reaction systems.

In one embodiment, within the predetermined time, the current value 1 and the current value 2 can only be compared one time. In another embodiment, within the predetermined time, the current value 1 and the current value 2 can be compared various of times. Within the predetermined time, when it is estimated that the amount of sample liquid on the working electrode has already satisfied the test requirement, the compare is complete and the concentration of analyte of interest in the sample liquid will be output.

A method of estimating if the supplied sample of liquid is sufficient, includes: providing a biosensor; applying a sample liquid to the biosensor; applying a voltage between the working electrode (103) and the counter electrode (105), measuring the electrical parameter 1 between the working electrode (103) and the counter electrode (105); turning off the electrical circuit connecting between the working electrode (103) and the counter electrode (105); applying a voltage between the working electrode (103) and the third electrode (107), measuring the electrical parameter 2 between the working electrode (103) and the third electrode (107); calculating the parameter 1 and the parameter 2, and comparing them with the predetermined threshold, then estimating if the amount of supplied sample liquid satisfies the test requirement or not. In another embodiment, the voltage is applied between the working electrode (103) and the third electrode (107), and the electrical parameter 2 is detected between the working electrode (103) and the third electrode (107). After shut off the electrical connection between the working electrode (103) and the third electrode (107), a voltage is applied between the working electrode (103) and the counter electrode (105), and the electrical parameter 1 is detected between the working electrode (103) and the counter electrode (105). The detecting voltages have different values basing on different electronic media, such as 0.25V, 0.4V or 0.6V et al.

EXAMPLE 1

A verification test to estimate if sample liquid with different concentrations of glucose is sufficiently applied.

A test is processed by applying blood samples, which have concentrations of glucose 60 mg/dl, 120 mg/dl, 280 mg/dl, 500 mg/dl, respectively, into biosensors of the present invention. For each concentration of glucose, 10 groups of blood samples have sufficient amount and can fulfil the test requirement while 10 other groups of blood samples have insufficient amount and cannot fulfil the test requirement. The test results are shown in tables 1-4 and FIGS. 6-9. The test results indicate that, when the amount of sample liquid is sufficient, the current values 1 and 2 respectively taken at the 5.0 second and the 5.1 second have a very little bias, which has a different rate less than 5%, and the diagram between the 5.0 second and the 5.1 second almost has no change. However, when the amount of sample liquid cannot fulfil the test requirement, the current values 1 and 2, respectively taken at the 5.0 second and the 5.1 second, have a very large bias, which has an absolute bias rate greater than 30% or even infinite, and the diagram between the 5.0 second and the 5.1 second presents an obvious steep peak. The test results indicate that, by using the current value 1 and the current value 2 produced by the biosensor of the present invention, and by comparing the current value 1 and the current value 2, it can be well reflect if the amount of applied sample liquid is sufficient or not, and the result will not be effected by the concentration of glucose in the sample liquid, therefore has a good stability.

TABLE 1

| Concentration of glucose (mg/dl) | Volume of applied sample liquid | Current value 1 taken from the working electrode or the counter electrode (tested at the 5th second) | Current value 2 taken from the working electrode or the third electrode (tested at the 5.1th second) | (Bias) | (Bias %) |
|---|---|---|---|---|---|
| 60 | insufficient | 0 | 19 | 19 | infinite |
| 60 | insufficient | 0 | 3 | 3 | infinite |
| 60 | insufficient | 0 | 1 | 1 | infinite |
| 60 | insufficient | 0 | 10 | 10 | infinite |
| 60 | insufficient | 0 | 5 | 5 | infinite |
| 60 | insufficient | 0 | 6 | 6 | infinite |
| 60 | insufficient | 0 | 2 | 2 | infinite |
| 60 | insufficient | 1 | 0 | −1 | −100.0% |
| 60 | insufficient | 0 | 6 | 6 | infinite |
| 60 | insufficient | 0 | 3 | 3 | infinite |
| 60 | sufficient | 156 | 159 | 3 | 1.9% |
| 60 | sufficient | 155 | 158 | 3 | 1.9% |
| 60 | sufficient | 156 | 159 | 3 | 1.9% |
| 60 | sufficient | 152 | 155 | 3 | 2.0% |
| 60 | sufficient | 153 | 156 | 3 | 2.0% |
| 60 | sufficient | 153 | 156 | 3 | 2.0% |
| 60 | sufficient | 153 | 155 | 2 | 1.3% |
| 60 | sufficient | 153 | 154 | 1 | 0.7% |
| 60 | sufficient | 152 | 154 | 2 | 1.3% |
| 60 | sufficient | 151 | 153 | 2 | 1.3% |

TABLE 2

| Concentration of glucose (mg/dl) | Volume of applied sample liquid | Current value 1 taken from the working electrode or the counter electrode (tested at the 5th second) | Current value 2 taken from the working electrode or the third electrode (tested at the 5.1th second) | (Bias) | (Bias %) |
|---|---|---|---|---|---|
| 120 | insufficient | 0 | 1 | 1 | infinite |
| 120 | insufficient | 0 | 2 | 2 | infinite |
| 120 | insufficient | 1 | 179 | 178 | 17800.0% |
| 120 | insufficient | 0 | 106 | 106 | infinite |
| 120 | insufficient | 0 | 3 | 3 | infinite |
| 120 | insufficient | 0 | 28 | 28 | infinite |
| 120 | insufficient | 0 | 2 | 2 | infinite |
| 120 | insufficient | 1 | 17 | 16 | 1600.0% |
| 120 | insufficient | 0 | 813 | 813 | infinite |
| 120 | insufficient | 0 | 339 | 339 | infinite |
| 120 | sufficient | 282 | 288 | 6 | 2.1% |
| 120 | sufficient | 290 | 296 | 6 | 2.1% |
| 120 | sufficient | 288 | 293 | 5 | 1.7% |
| 120 | sufficient | 289 | 294 | 5 | 1.7% |
| 120 | sufficient | 282 | 287 | 5 | 1.8% |
| 120 | sufficient | 285 | 291 | 6 | 2.1% |
| 120 | sufficient | 279 | 285 | 6 | 2.2% |
| 120 | sufficient | 286 | 291 | 5 | 1.7% |
| 120 | sufficient | 280 | 284 | 4 | 1.4% |
| 120 | sufficient | 278 | 282 | 4 | 1.4% |

TABLE 3

| Concentration of glucose (mg/dl) | Volume of applied sample liquid | Current value 1 taken from the working electrode or the counter electrode (tested at the 5.0th second) | Current value 2 taken from the working electrode or the third electrode (tested at the 5.1th second) | (Bias) | (Bias %) |
|---|---|---|---|---|---|
| 280 | insufficient | 1 | 4 | 3 | 300.0% |
| 280 | insufficient | 0 | 0 | 0 | infinite |
| 280 | insufficient | 0 | 370 | 370 | infinite |
| 280 | insufficient | 0 | 132 | 132 | infinite |
| 280 | insufficient | 0 | 1 | 1 | infinite |
| 280 | insufficient | 0 | 1 | 1 | infinite |
| 280 | insufficient | 0 | 1 | 1 | infinite |
| 280 | insufficient | 0 | 1 | 1 | infinite |
| 280 | insufficient | 0 | 528 | 528 | infinite |
| 280 | sufficient | 521 | 533 | 12 | 2.3% |
| 280 | sufficient | 527 | 539 | 12 | 2.3% |
| 280 | sufficient | 511 | 523 | 12 | 2.3% |
| 280 | sufficient | 518 | 530 | 12 | 2.3% |
| 280 | sufficient | 515 | 528 | 13 | 2.5% |
| 280 | sufficient | 505 | 517 | 12 | 2.4% |
| 280 | sufficient | 512 | 524 | 12 | 2.3% |
| 280 | sufficient | 506 | 518 | 12 | 2.4% |
| 280 | Sufficient | 512 | 525 | 13 | 2.5% |
| 280 | Sufficient | 496 | 510 | 14 | 2.8% |

TABLE 4

| Concentration of glucose (mg/dl) | Volume of applied sample liquid | Current value 1 taken from the working electrode or the counter electrode (tested at the 5th second) | Current value 2 taken from the working electrode or the third electrode (tested at the 5.1th second) | (Bias) | (Bias %) |
|---|---|---|---|---|---|
| 500 | insufficient | 0 | 0 | 0 | infinite |
| 500 | insufficient | 0 | 2130 | 2130 | infinite |
| 500 | insufficient | 1 | 1 | 0 | 0.0% |
| 500 | insufficient | 0 | 9 | 9 | infinite |
| 500 | insufficient | 0 | 0 | 0 | infinite |
| 500 | insufficient | 0 | 538 | 538 | infinite |
| 500 | insufficient | 0 | 2960 | 2960 | infinite |
| 500 | insufficient | 0 | 3653 | 3653 | infinite |
| 500 | insufficient | 0 | 3895 | 3895 | infinite |
| 500 | insufficient | 0 | 1683 | 1683 | infinite |
| 500 | sufficient | 893 | 930 | 37 | 4.1% |
| 500 | sufficient | 887 | 926 | 39 | 4.4% |
| 500 | sufficient | 881 | 920 | 39 | 4.4% |
| 500 | sufficient | 881 | 915 | 34 | 3.9% |
| 500 | sufficient | 904 | 942 | 38 | 4.2% |
| 500 | sufficient | 908 | 940 | 32 | 3.5% |
| 500 | sufficient | 899 | 931 | 32 | 3.6% |
| 500 | sufficient | 900 | 932 | 32 | 3.6% |
| 500 | sufficient | 887 | 924 | 37 | 4.2% |
| 500 | sufficient | 889 | 922 | 33 | 3.7% |

In another embodiment, the current value 1 and the current value 2 are circularly tested and compared as soon as the sample liquid is applied. When the comparison of the current value 1 and the current value 2 matches the predetermined threshold that indicates the amount of supplied sample liquid is sufficient, the comparison of the current value 1 and the current value 2 is stopped. Immediately the concentration of the analyte of interest in the sample liquid is detected, and an accurate concentration of the analyte of interest is output. On the contrary, within the predetermined time, when the comparison of the current value 1 and the current value 2 does not match the predetermined threshold that indicates the amount of applied sample liquid is sufficient, the electrical meter outputs a message of insufficient amount of sample liquid. The predetermined time is 5 seconds, 10 seconds or any other proper time.

EXAMPLE 2

Figure 10:
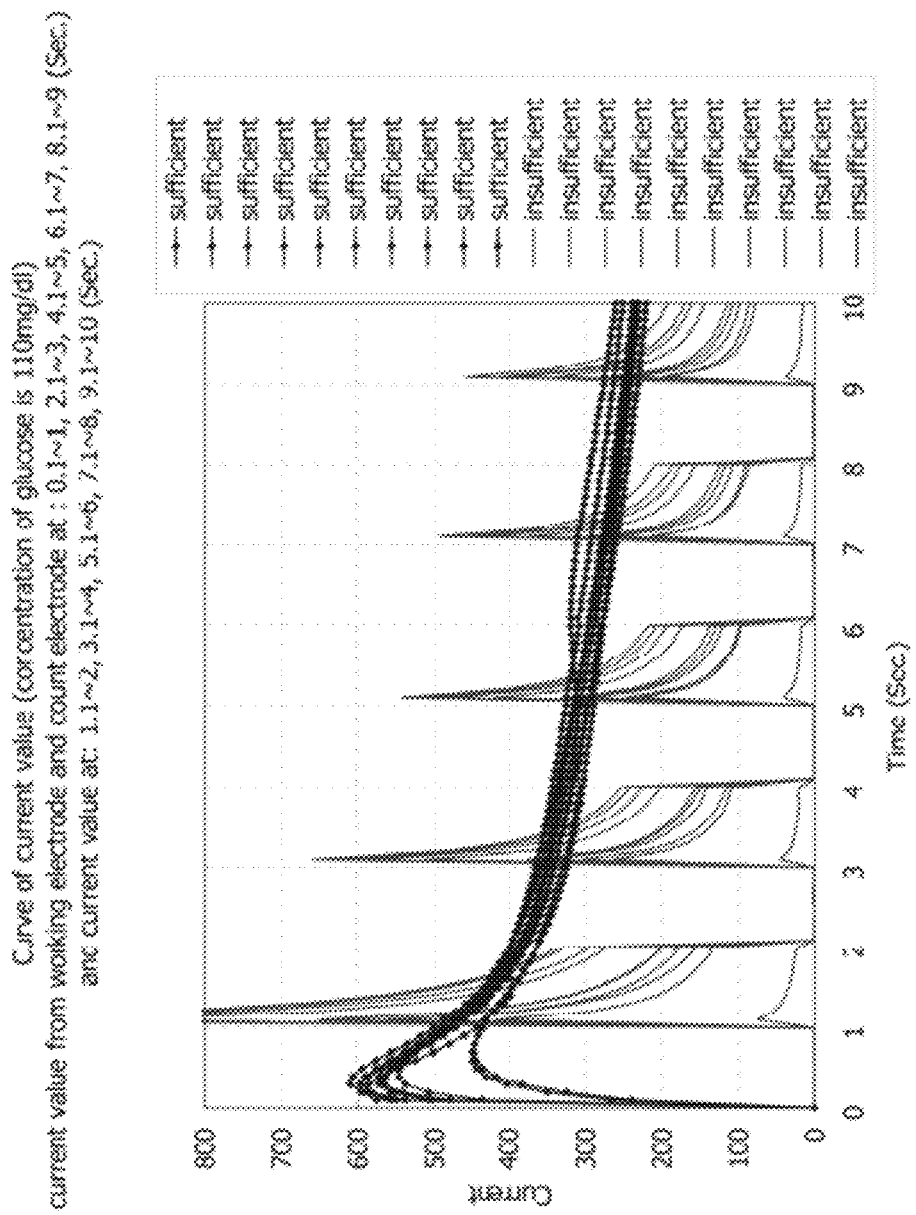
FIG. 10 is a graph showing changes in response current tested by switching test methodology when the concentration of glucose is 110 mg/dl.

A verification test to estimate if samples liquid with different concentrations of glucose are sufficiently applied by a method of circular test A test is processed by applying blood samples, which have concentrations of glucose 110 mg/dl, 380 mg/dl, respectively, into a biosensor of the present invention. The test results are shown in table 5 and FIG. 10. To compare respectively the current values 1 taken at the 1.0 second, the 3.0 second and the 5.0 second with the current values 2 accordingly taken at the 1.1 second, the 3.1 second and the 5.1 second. The parameter for estimating if the amount of sample liquid is sufficient is set as 10%. When the absolute bias rate between the current value 1 and the current value 2 is less than 10%, it is estimated that the amount of sample liquid is sufficient, or else, it is estimated that the amount of sample liquid is insufficient. The test results indicate that, within the predetermined time, when the amounts of sample liquid are sufficient, the absolute bias rate at the test point of time is less than 10%. Within the predetermined time, if the absolute current bias rate at the test point of time is larger than the predetermined parameter, it indicates that the amounts of sample liquid are insufficient.

can fulfil the test requirement, the electrical detecting system will convert the current value between the working electrode 103 and the counter electrode into the concentration of an analyte of interest in the tested sample liquid.

TABLE 5

| Glucose concentration (mg/dl) | Volume of sample liquid | Sampled value of current 1 (1.0S) | Sampled value of current 2 (1.1S) | Bias | Bias rate % | Sampled value of current 1 (3.0S) | Sampled value of current 2 (3.1S) | Bias | Bias rate % | Sampled value of current 1 (5.0S) | Sampled value of current 2 (5.1S) | Bias | Bias rate % |
|---|---|---|---|---|---|---|---|---|---|---|---|---|---|
| 110 | SU* | 436 | 432 | −4 | −0.9% | 324 | 323 | −1 | −0.3% | 289 | 289 | 0 | 0.0% |
| 110 | SU | 444 | 434 | −10 | −2.3% | 365 | 364 | −1 | −0.3% | 315 | 313 | −2 | −0.6% |
| 110 | SU | 485 | 473 | −12 | −2.5% | 347 | 346 | −1 | −0.3% | 306 | 305 | −1 | −0.3% |
| 110 | SU | 490 | 477 | −13 | −2.7% | 352 | 350 | −2 | −0.6% | 314 | 312 | −2 | −0.6% |
| 110 | SU | 437 | 430 | −7 | −1.6% | 330 | 325 | −5 | −1.5% | 299 | 294 | −5 | −1.7% |
| 110 | SU | 501 | 488 | −13 | −2.6% | 358 | 356 | −2 | −0.6% | 315 | 314 | −1 | −0.3% |
| 110 | SU | 488 | 477 | −11 | −2.3% | 351 | 350 | −1 | −0.3% | 312 | 312 | 0 | 0.0% |
| 110 | SU | 472 | 461 | −11 | −2.3% | 340 | 339 | −1 | −0.3% | 309 | 310 | 1 | 0.3% |
| 110 | SU | 485 | 476 | −9 | −1.9% | 363 | 363 | 0 | 0.0% | 325 | 324 | −1 | −0.3% |
| 110 | SU | 477 | 465 | −12 | −2.5% | 341 | 338 | −3 | −0.9% | 296 | 295 | −1 | −0.3% |
| 110 | INS* | 0 | 75 | 75 | INF* | 0 | 45 | 45 | INF | 0 | 40 | 40 | INF |
| 110 | INS | 0 | 417 | 417 | INF | 0 | 264 | 264 | INF | 0 | 229 | 229 | INF |
| 110 | INS | 0 | 637 | 637 | INF | 0 | 373 | 373 | INF | 0 | 306 | 306 | INF |
| 110 | INS | 1 | 1180 | 1179 | 117900.0% | 1 | 631 | 630 | 63000.0% | 1 | 511 | 510 | 51000.0% |
| 110 | INS | 1 | 650 | 649 | 64900.0% | 1 | 375 | 374 | 37400.0% | 1 | 320 | 319 | 31900.0% |
| 110 | INS | 0 | 942 | 942 | INF | 0 | 512 | 512 | INF | 0 | 419 | 419 | INF |
| 110 | INS | 0 | 560 | 560 | INF | 0 | 352 | 352 | INF | 0 | 292 | 292 | INF |
| 110 | INS | 1 | 1225 | 1224 | 122400.0% | 0 | 658 | 658 | INF | 1 | 543 | 542 | 54200.0% |
| 110 | INS | 0 | 562 | 562 | INF | 0 | 305 | 305 | INF | 0 | 247 | 247 | INF |
| 110 | INS | 0 | 1088 | 1088 | INF | 0 | 585 | 585 | INF | 0 | 481 | 481 | INF |
| 380 | SU | 396 | 1385 | −11 | −0.8% | 940 | 932 | −8 | −0.9% | 788 | 786 | −2 | −0.3% |
| 380 | SU | 502 | 1473 | −29 | −1.9% | 1011 | 1000 | −11 | −1.1% | 848 | 844 | −4 | −0.5% |
| 380 | SU | 514 | 1476 | −38 | −2.5% | 986 | 975 | −11 | −1.1% | 837 | 829 | −8 | −1.0% |
| 380 | SU | 1590 | 1552 | −38 | −2.4% | 1010 | 999 | −11 | −1.1% | 836 | 832 | −4 | −0.5% |
| 380 | SU | 1518 | 1487 | −31 | −2.0% | 969 | 959 | −10 | −1.0% | 801 | 797 | −4 | −0.5% |
| 380 | SU | 1622 | 1584 | −38 | −2.3% | 1012 | 1007 | −5 | −0.5% | 843 | 843 | 0 | 0.0% |
| 380 | SU | 1597 | 1560 | −37 | −2.3% | 1024 | 1015 | −9 | −0.9% | 861 | 857 | −4 | −0.5% |
| 380 | SU | 1464 | 1432 | −32 | −2.2% | 1020 | 1018 | −2 | −0.2% | 897 | 897 | 0 | 0.0% |
| 380 | SU | 1532 | 1497 | −35 | −2.3% | 992 | 982 | −10 | −1.0% | 840 | 837 | −3 | −0.4% |
| 380 | SU | 1443 | 1412 | −31 | −2.1% | 1043 | 1028 | −15 | −1.4% | 868 | 860 | −8 | −0.9% |
| 380 | SU | 1337 | 1521 | 184 | 13.8% | 877 | 915 | 38 | 4.3% | 745 | 772 | 27 | 3.6% |
| 380 | SU | 1537 | 1692 | 155 | 10.1% | 913 | 952 | 39 | 4.3% | 779 | 808 | 29 | 3.7% |
| 380 | INS | 0 | 694 | 694 | INF | 0 | 367 | 367 | INF | 0 | 283 | 283 | INF |
| 380 | INS | 0 | 2873 | 2873 | INF | 0 | 1579 | 1579 | INF | 0 | 1254 | 1254 | INF |
| 380 | INS | 0 | 3925 | 3925 | INF | 0 | 2449 | 2449 | INF | 1 | 1961 | 1960 | 196000.0% |
| 380 | INS | 3 | 3932 | 3929 | 130966.7% | 12 | 2842 | 2830 | 23583.3% | 30 | 2268 | 2238 | 7460.0% |
| 380 | INS | 0 | 1996 | 1996 | INF | 0 | 1040 | 1040 | INF | 0 | 847 | 847 | INF |
| 380 | INS | 0 | 2964 | 2964 | INF | 0 | 1625 | 1625 | INF | 0 | 1300 | 1300 | INF |
| 380 | INS | 0 | 2251 | 2251 | INF | 0 | 1214 | 1214 | INF | 0 | 964 | 964 | INF |
| 380 | INS | 0 | 3582 | 3582 | INF | 0 | 2028 | 2028 | INF | 1 | 1666 | 1665 | 166500.0% |

*SU: sufficient   INS: insufficient   INF: infinite

The time interval for switching the test of the current value 2 to the test of the current value 1 is controlled within 1 second, and preferably to be 0.1 second.

In another embodiment, the invention is relative to a method of using the biosensor of the invention to detect the concentration of an analyte in the sample liquid. The method includes: inserting the biosensor into an electrical detecting system and connecting the biosensor with the electrical detecting system via the connecting conductors; applying a sample liquid with analyte of interest to a sample introducing port 224 of the biosensor; detecting the current value 1 between the working electrode 103 and the counter electrode 105 and the current value 2 between the working electrode 103 and the third electrode 107; comparing the current value 1 and the current value 2, if it is estimated that the volume of applied sample is insufficient, the electrical detecting system outputs an error of insufficient sample liquid and an invalid test; if it is estimated that the amount of applied sample liquid

EXAMPLE 3

Test result by using the biosensor of the present invention to test the concentration of glucose in blood.

Figure 11:
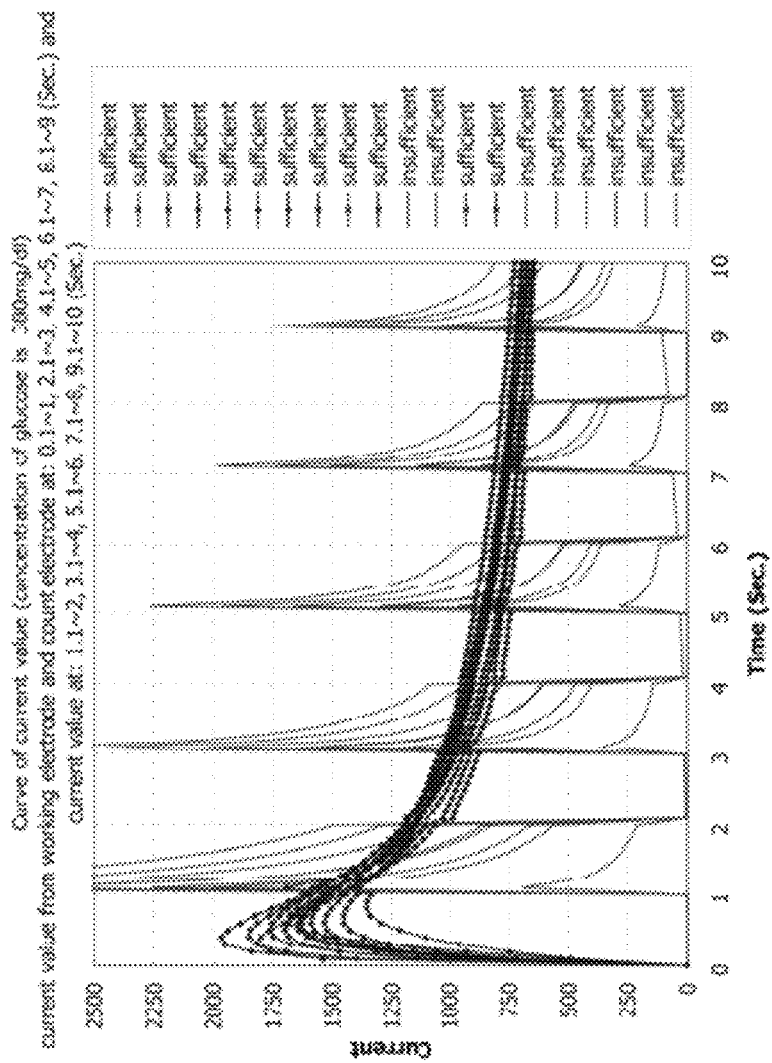
FIG. 11 is a graph showing changes in response current tested by switching test methodology when the concentration of glucose is 380 mg/dl.
Figure 12:
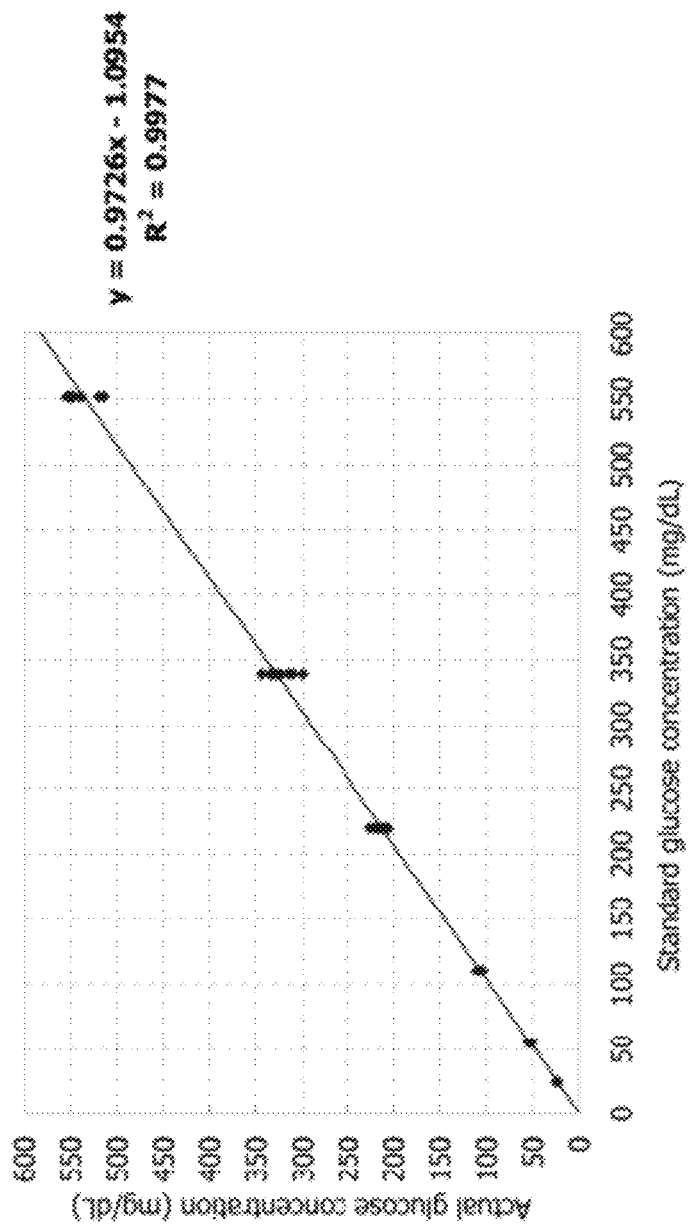
FIG. 12 is an accuracy analytical graph of the concentration of glucose detected by a biosensor of the present invention.

Turn on a glucose meter (for example the ON CALL™ glucose meter provided by Acon company), and maintain the meter in testing status. Insert the biosensor of the present invention into the meter, and test a various of blood samples with different concentrations of glucose, respectively. The test results are shown in table 7 and FIG. 11.

TABLE 6

| Actual glucose concentration (mg/dl) | 24.9 | 54.8 | 110.7 | 219.6 | 339.2 | 551.6 |
|---|---|---|---|---|---|---|
| Standard glucose concentration (mg/dl) | 24.3 | 53.6 | 102.4 | 206.1 | 318.3 | 521.4 |

The experiment indicates that the test with a biosensor of the present invention has a high accuracy.

Technical persons in the art relative to the present invention may make a lot of changes basing on the disclosure of the present invention, all the changes belong to the content of the present invention. For example, the invention can be used in testing an analyte of interest in any sample liquid, and the analyte of interest can be any substances in addition to glucose. In addition, the parameters of the present invention taken between the working electrode 103 and the counter electrode 105 or the working electrode 103 and the third electrode 107 are not limited to the current value or the sampled value of current. The predetermined threshold in the above embodiments can be any proper values.

We claim:

1. A method of estimating if sufficient sample is supplied, including:
    providing a biosensor, the biosensor including an insulative substrate, a reaction layer, a covering layer and a sample introducing port, the insulative substrate having an electrode system on a surface thereof, the electrode system at least including a working electrode, a counter electrode and a third electrode, wherein the third electrode is nearer to the sample introducing port than the counter electrode, the reaction layer at least covering the working electrode;
    applying a sample liquid to the biosensor;
    applying a voltage between the working electrode (103) and the counter electrode (105), and measuring a first current value between the working electrode (103) and the counter electrode (105);
    turning off the electrical circuit connecting the working electrode (103) and the counter electrode (105);
    applying a voltage between the working electrode (103) and the third electrode (107), and measuring a second current value between the working electrode (103) and the third electrode (107);
    comparing a bias between the first current value and the second current value them with the a predetermined threshold, wherein (i) if the bias is greater than the predetermined threshold, estimating that the supplied sample liquid cannot meet the test requirement, and (ii) if the bias is less than the predetermined threshold, then estimating that the supplied sample liquid can meet the test requirement.

2. The method according to claim 1, wherein the first current value and the second current value are detected within one second.

3. The method according to claim 2, wherein the first current value and the second current value are detected within 0.1 second.

4. The method according to claim 1, wherein the first current value and the second current value are circularly detected and compared within a predetermined time.

5. The method according to claim 4, wherein the if the estimation is that the sample liquid cannot meet the test requirement, then outputting an error message of insufficient sample liquid; and if the estimation is that the sample liquid can meet the test requirement, then stopping comparing the bias rate to the threshold and outputting a message of sufficient sample liquid.

6. The method according to claim 4, wherein if the estimation is that the sample liquid cannot meet the test requirement, then outputting an error message of insufficient sample liquid; and if the estimation is that the sample liquid can meet the test requirement, then stopping comparing the bias rate to the threshold and outputting a message of sufficient sample liquid.

7. A method of estimating if sufficient sample is supplied, including:
    providing a biosensor, the biosensor including an insulative substrate, a reaction layer, a covering layer and a sample introducing port, the insulative substrate having an electrode system on a surface thereof, the electrode system at least including a working electrode, a counter electrode and a third electrode, wherein the third electrode is nearer to the sample introducing port than the counter electrode, the reaction layer at least covering the working electrode;
    applying a sample liquid to the biosensor;
    applying a voltage between the working electrode (103) and the counter electrode (105), and measuring a first current value between the working electrode (103) and the counter electrode (105);
    turning off the electrical circuit connecting the working electrode (103) and the counter electrode (105);
    applying a voltage between the working electrode (103) and the third electrode (107), and measuring a second current value between the working electrode (103) and the third electrode (107);
    comparing a bias rate between the current value 1 and the current value 2 with a predetermined threshold, wherein (i) if the bias rate is greater than the predetermined threshold, then estimating that the supplied sample liquid cannot meet the test requirement, and (ii) if the bias rate is less than the predetermined threshold, then estimating that the supplied sample liquid can meet the test requirement.

8. The method according to claim 7, wherein the first current value and the second current value are detected within one second.

9. The method according to claim 8, wherein the first current value and the second current value are detected within 0.1 second.

10. The method according to claim 7, wherein the first current value and the second current value are circularly detected and compared within a predetermined time.

* * * * *